United States Patent [19]
Cowan

[11] Patent Number: 5,167,611
[45] Date of Patent: Dec. 1, 1992

[54] PENILE IMPLANT WITH LENGTHENING CYLINDER

[75] Inventor: Timothy Cowan, Andover, Minn.

[73] Assignee: Mentor Corporation, Santa Barbara, Calif.

[21] Appl. No.: 733,426

[22] Filed: Jul. 22, 1991

[51] Int. Cl.⁵ ............................................... A61F 2/26
[52] U.S. Cl. ....................................................... 600/40
[58] Field of Search ........................................... 128/79

[56] References Cited

U.S. PATENT DOCUMENTS

| | | | |
|---|---|---|---|
| 4,267,829 | 5/1981 | Burton et al. | 128/79 |
| 4,566,446 | 1/1986 | Fogarty | 128/79 |
| 4,730,607 | 3/1988 | Fischell | 128/79 |
| 4,881,530 | 11/1989 | Frick | 128/79 |

*Primary Examiner*—Cary E. O'Connor
*Attorney, Agent, or Firm*—Blakely, Sokoloff, Taylor & Zafman

[57] ABSTRACT

A penile prosthesis with a two piece inflatable cylinder that provides significant lengthwise expansion of a male penis. The cylinder has an inflatable bellows attached to an inflatable member and a sheath that extends from a base member. The bellows is attached to the base member and the sheath is connected to the inflatable member, such that the sheath will stretch when the bellows is inflated. The sheath surrounds the bellows. The sheath is constructed from an elastic material that can expand up to 100% of its original length. The inflatable member and bellows are connected to a pump which transfers fluid between a reservoir and the cylinder. When fluid is pumped into the cylinder, the bellows and inflatable member are inflated and the sheath is expanded, allowing the inflatable member to move into an elongated position. When the cylinder is inflated the sheath is in tension, wherein the sheath will pull the inflatable member back into a compact position when the bellows is deflated.

9 Claims, 4 Drawing Sheets

FIG. 1

PENILE IMPLANT WITH LENGTHENING CYLINDER

BACKGROUND OF THE INVENTION

1. Field of the Invention

The present invention relates to an implantable penile prostheses, and more particularly to an extendable penile prosthesis.

2. Description of Related Art

Penile prosthesis are typically implanted into a patient to overcome erectile impotence. Most penile prosthesis have inflatable cylinders that are surgically implanted into the corpora cavernosa regions of the penis. The cylinders are typically connected to a pump that transfers fluid from a reservoir to the cylinders.

Prior penile prosthesis include the devices described and shown in U.S. Pat. No. 4,009,711 issued to Uson, U.S. Pat. No. 3,954,102 issued to Buuck, U.S. Pat. No. 4,235,227 issued to Yamanaka and U.S. Pat. No. 4,726,360 issued to Trick et al, which disclose simple inflatable tube-like cylinders that expand when pumped with a working fluid. The cylinders are typically constructed from a nondistensible material and are blown up in the same manner as the inner tube of a tire. Unfortunately, these devices do not provide much lengthwise expansion of the penis, which is part of the natural movement of a normal penis during erection.

U.S. Pat. No. 4,730,607 issued to Fischell and U.S. Pat. No. 4,718,410 issued to Hakky, disclose an inflatable cylinder having bellows which provides significant elongation of the prosthesis and consequently, of the penis, when inflated. However, there is a problem with the retraction of the bellows in these devices after use because the rate of retraction is dependent only upon the memory of the bellows material such that the spring rate of the bellows is low. Therefore, the cylinder of these devices does not readily contract when the operating fluid is removed from the penis pendulus area of the implant. Such a prosthesis may require manual manipulation to fully return the penis into a natural flaccid position. Therefore it would be desirable to have an inflatable penile prosthesis cylinder that provides considerable lengthwise expansion and readily contracts into a natural flaccid position.

SUMMARY OF THE INVENTION

The present invention is a penile prosthesis with an inflatable cylinder that provides significant lengthwise expansion of a male penis. The cylinder has a proximal end which is generally a rigid, solid, tapering cylindrical base member and a distal end comprising an inflatable member. The cylinder wall comprises, in its midportion between the distal and proximal ends, an inflatable bellows which attaches at one end to the base member and the other end to the inflatable member. Disposed over the bellows is a sheath that similarly attaches to the base member and inflatable member. When the bellows is in its retracted position, the sheath is likewise relaxed and not stretched. When the bellows is expanded during inflation thereof, the sheath will stretch. The sheath is constructed from an elastic material which can typically expand up to 100% of its original length.

The inflatable cylinder is connected to a pump, which transfers fluid between a reservoir and the cylinder. When fluid is pumped into the cylinder, the bellows and inflatable member are inflated and the sheath is expanded, allowing the distal end to move distally into an elongated position. When the cylinder is inflated the sheath is under tension. When deflated, the sheath will pull the distal end back into a compact position. The spring rate of the sheath is relatively high, so that the cylinder readily contracts the penis into a natural flaccid position.

Therefore it is an object of this invention to provide a penile prosthesis which has an inflatable cylinder that provides significant penile expansion.

It is also an object of this invention to provide a penile prosthesis which has an inflatable cylinder that provides significant penile expansion and readily contracts the penis into a natural flaccid position.

BRIEF DESCRIPTION OF THE DRAWINGS

The objects and advantages of the present invention will become more readily apparent to those skilled in the art after reviewing the following detailed description and accompanying drawings, wherein.

DETAILED DESCRIPTION OF THE INVENTION

Figure 1:
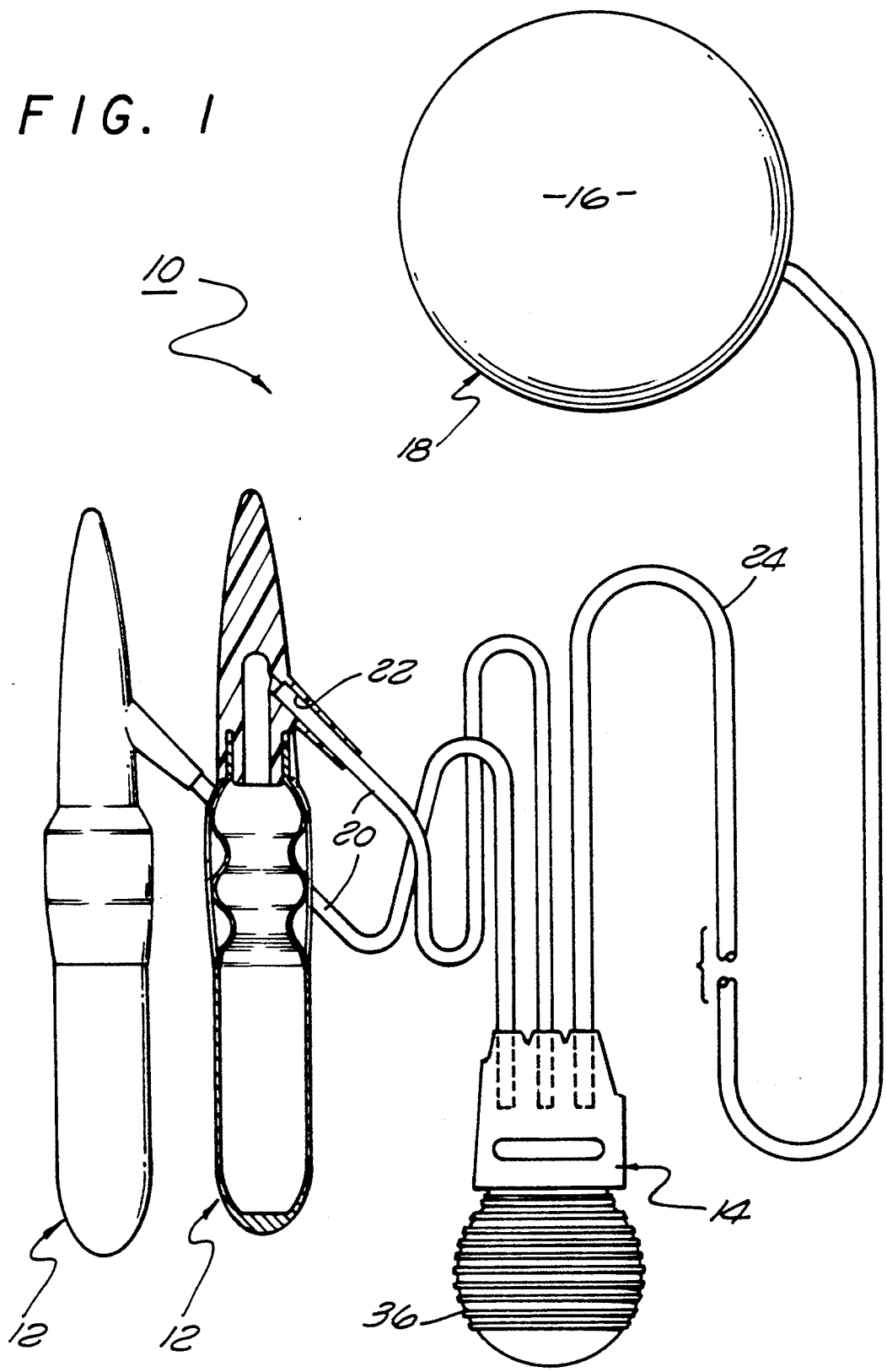
FIG. 1 is a side view of a three piece penile prosthesis of the present invention.

Referring to the drawings more particularly by reference numbers, FIG. 1 shows a penile implant 10 of the present invention. The implant 10 has a pair of inflatable cylinders 12 attached to a pump 14, which transfers fluid 16 between a reservoir 18 and the cylinders 12. The pump 14 is connected to the cylinders 12 by a pair of first tubes 20 that extend into ports 22 formed in the cylinders 12. The reservoir 18 is attached to the pump 14 by a second tube 24. The tubes 20 and 24 are preferably constructed from either nylon or a silicone rubber, which provide flexibility and protection from contamination. In the preferred embodiment, the reservoir 18 is constructed from a polyurethane that is flexible enough to be implanted into the pelvic cavity of a patient and compatible with a human body without substantial risk of rejection in a typical patient. The elastic nature of the reservoir 18 also allows the bag 18 to contract and expand when fluid is transferred to and from the cylinders 12.

The pump 14 is preferably constructed from a silicone elastomer, which can be easily squeezed by the user and has enough resiliency to return to the original state when released. The pump 14 has a valve (not shown) which allows one directional fluid flow into the cylinders 12, when the pump housing 26 is squeezed in and out by the user. The valve prevents fluid from flowing out of the cylinders 12 when the cylinders 12 are in an extended position. Manual manipulation of the pump 14 can open up the valve, so that fluid can flow from the cylinders 12 back to the reservoir 18.

Figure 2:
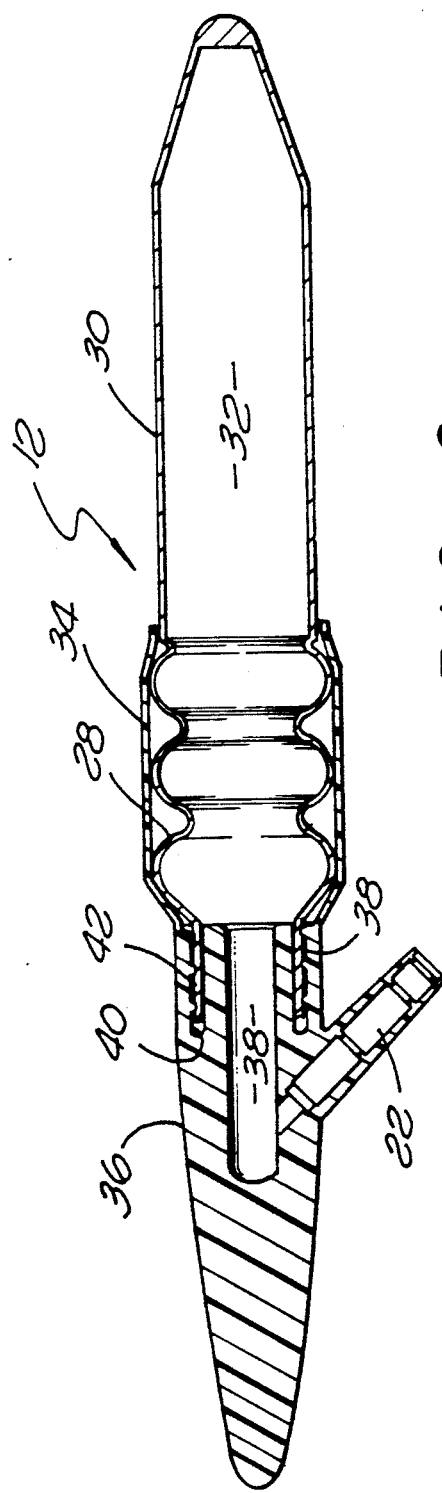
FIG. 2 is an enlarged side view of an inflatable cylinder of the penile prosthesis of FIG. 1, shown in a retracted position.
Figure 3:
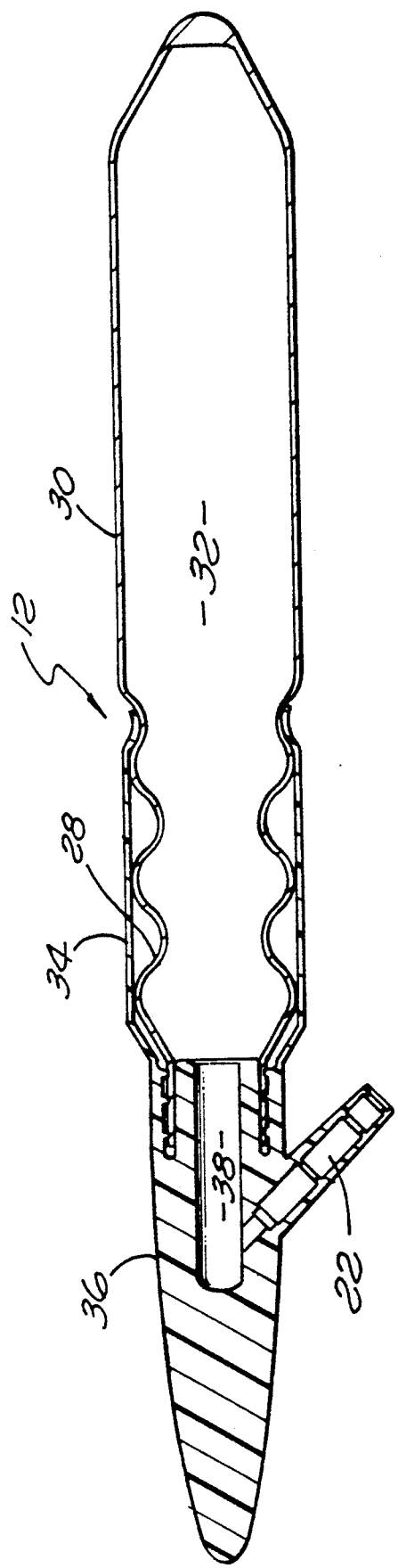
FIG. 3 is a side view of the inflatable cylinder of FIG. 2, shown in an extended position.
Figure 4:
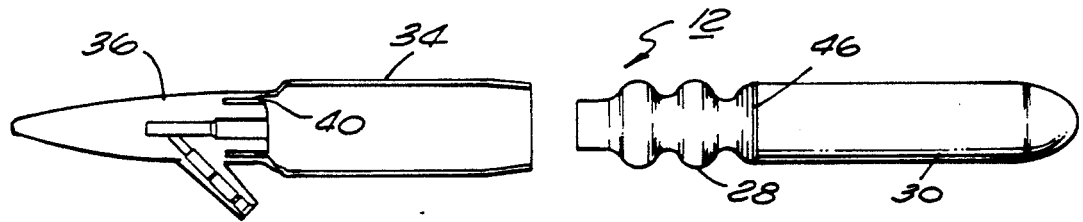
FIG. 4 is a side view of a two piece inflatable cylinder having a bellows attached to an inflatable member and a sheath extending from a base member.

FIGS. 2 and 3 show a preferred embodiment of the cylinder 12. The cylinder 12 has a bellows 28 attached to an inflatable member 30. The inflatable member 30 and bellows 28 have an inner cavity 32 that can be filled with fluid. The bellows 28 is surround on its exterior by an elastic sheath 34 which extends from a base member 36, and is attached to the inflatable member 30 connecting the inflatable member 30 to the base 36. The base member 36 is constructed from a silicone elastomer and is rigid enough to anchor the cylinder 12 into the root end of the corpus cavernosum. The base member 36 also has a bore 39 that provides fluid communication between the inner cavity 32 and the port 22. The port 22 and bore 39 allow fluid to flow between the inner cavity 32 and the pump 14.

FIG. 2 shows the cylinder 12 when the fluid within the inflatable member 30 and bellows 28 is at a relative zero pressure. Operation of the pump 14 causes the fluid pressure within the cylinder 12 to increase, so that the bellows 28 expands and the inflatable member 30 moves in the axial direction, as shown in FIG. 3. The inflatable member 30 is preferably constructed from a distensible material such as polyurethane between 0.013 and 0.019 inches thick. The distensible material allows the inflatable member 30 to expand and grow in both the axial and radial directions, thereby increasing the length and girth of the penis pendulum.

In the preferred embodiment the bellows 28 is constructed from a silicone elastomer that allows the bellows 28 to expand when the fluid reaches a predetermined pressure. The sheath 34 is preferably constructed from a silicone elastomer that is approximately 0.015 inches thick and can be stretched up to 100% of the unstressed length. The sheath 34 has a resilient memory and a high spring rate, so that when the fluid pressure within the cylinder 12 is reduced, the sheath 34 pulls the inflatable member 30 toward the base 36 until the cylinder 12 is in the retracted position shown in FIG. 2.

Figure 5:
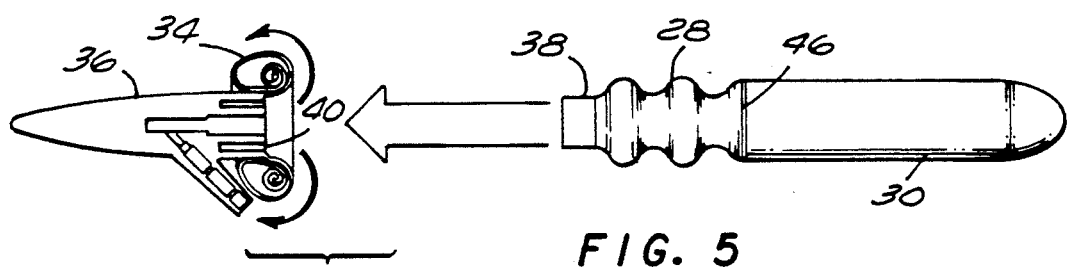
FIG. 5 is a side view of the two piece cylinder of FIG. 4 showing the sheath rolled up on the base member.
Figure 6:
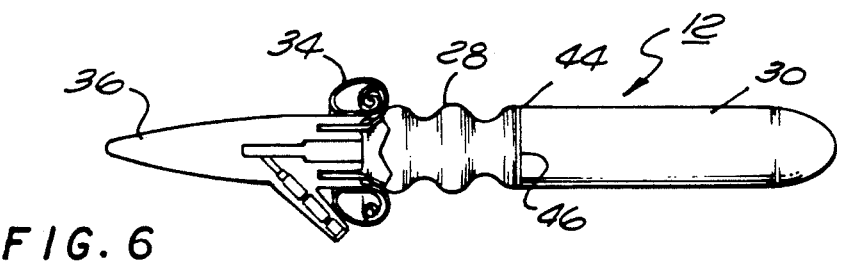
FIG. 6 is a side view of the two piece cylinder, wherein the bellows is attached to the base member.
Figure 7:
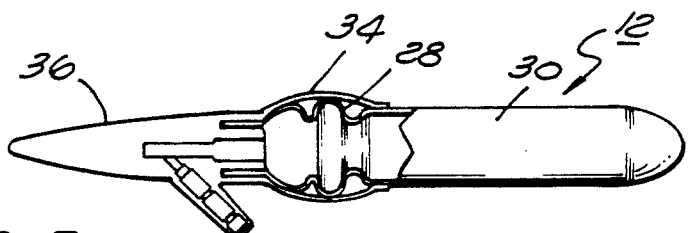
FIG. 7 is a side view of the two piece cylinder, wherein the bellows are super-retracted under vacuum and the sheath is unrolled onto the bellows and bonded to the inflatable member.
Figure 8:
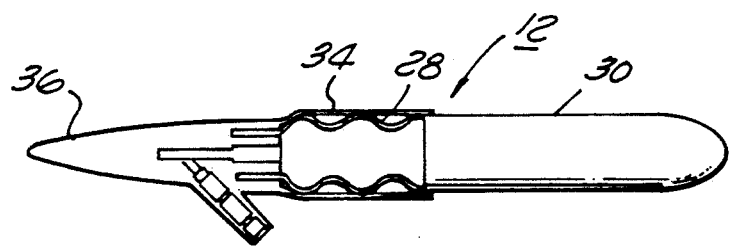
FIG. 8 is a side view of the two piece cylinder of FIG. 7 with the bellows and sheath in a normal relaxed arrangement and the inflatable member attached to the base member.

FIGS. 4-8 show a preferred method of assembling the cylinder 12. The cylinder 12 initially comprises two pieces, wherein the bellows 28 is attached to the inflatable member 30 and the sheath 34 extends from the base member 36. As shown in FIGS. 5 and 6, the sheath 34 is rolled up and a stem 38 of the bellows 28 is inserted into a groove 40 in the base 36. As shown more clearly in FIGS. 2 and 3, the groove 40 has protrusions 42 that pinch the stem 38, so that the bellows 28 cannot be easily removed from the base 28. The protrusions 42 also seal the inner cavity 32 from the area between the bellows 28 and the sheath 34. A vacuum is then created in the inner cavity 32 to contract the bellows 28 into a compressed position as shown in FIG. 7. An uncured adhesive 44, preferably a fumed silica, is placed on an annular groove 46 formed at the interface of the bellows 28 and the inflatable member 30. The sheath 34 is then unrolled and pulled over the bellows 28. The cylinder 12 is left in that state until the adhesive 44 cures and bonds the sheath 34 to the inflatable member 30. The vacuum is then removed so that the bellows 28 returns to the normal position shown in FIG. 8.

Figure 9:
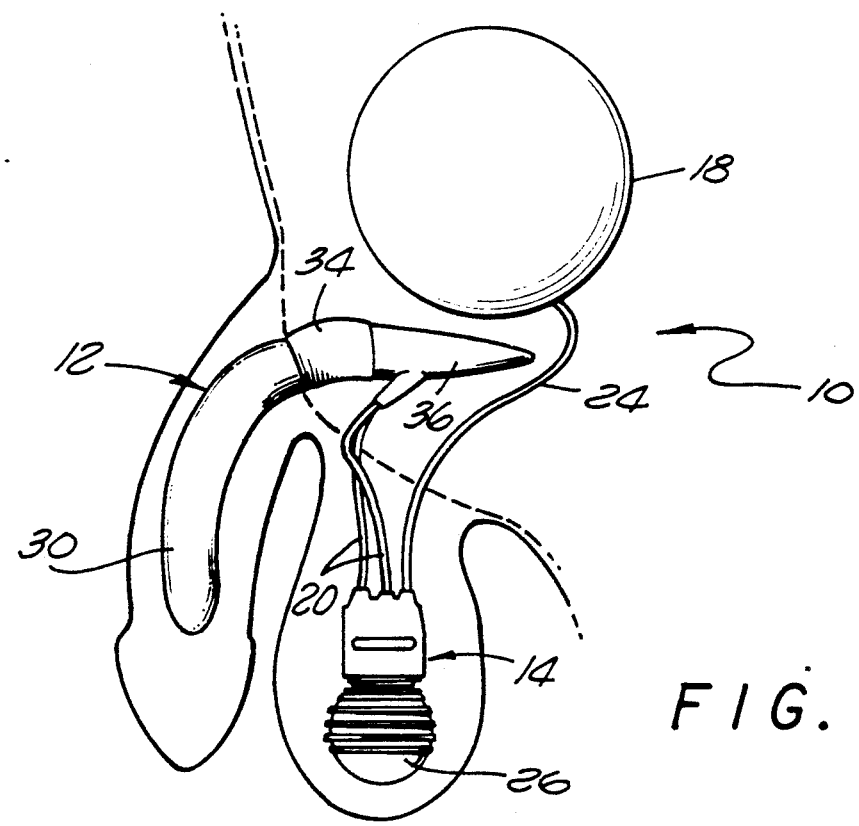
FIG. 9 is a side view of the penile implant of the present invention implanted into a patient, wherein the cylinder is in a retracted/flaccid position.

FIG. 9 shows a penile prosthesis 10 of the present invention implanted into a patient. Installation of the prosthesis 10 can be performed by any surgical procedure known in the art. The preferred method is to make an incision at the pelvic bone near the scrotum. The corpus cavernosa are then dilated and the cylinders 12 are inserted within the penis. Although two cylinders are shown, it is to be understood that only one cylinder 12 can be used in the present invention. The pump 14 is placed into the scrotal sac and the reservoir 18 is inserted into the abdomen. The cylinders 12 are placed within the penis such that the bellows 28 are completely within the pelvic cavity when the penis is in the flaccid position. In this manner the bellows 28 are not physically apparent to the touch when the penis is in the normally flaccid position.

Figure 10:
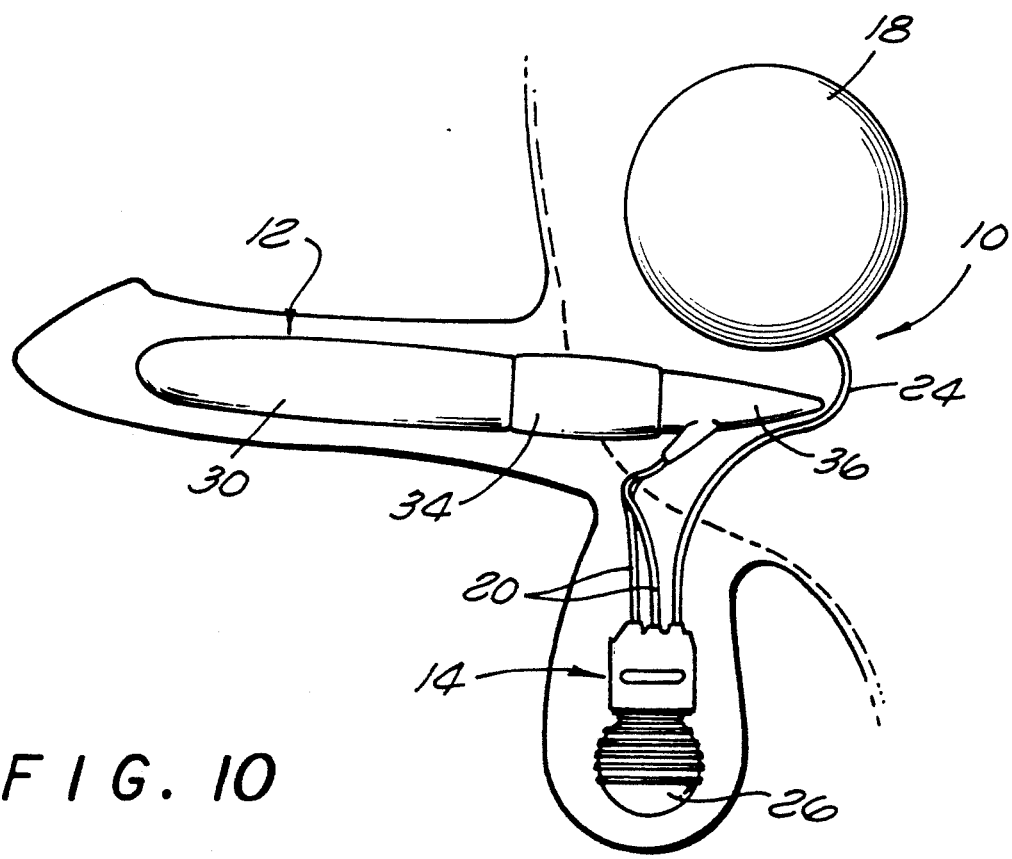
FIG. 10 is a side view similar to FIG. 9, showing the cylinder in an pressurized/extended position.

To operate the prosthesis 10, the user squeezes the pump 14 inside the scrotal sac to increase the fluid pressure within the cylinder 12. The pumping action causes the inflatable member 30 and bellows 28 to expand, thereby increasing the length and girth of the penis. In the preferred embodiment the operating pressure is approximately 12 psi. The amount of extension is approximately 3 cm and the amount of increased girth is approximately 30%, both dimensions depending upon the anatomical proportions of the patient. The yield pressure of the sheath 34 is approximately 12 psi, such that the cylinder 12 does not create significant length extension until the yield pressure is obtained within inner cavity 32. This construction prevents lengthening of the penis upon accidental squeezing of the pump 14. When the desired length is achieved, the pumping operation is desisted, wherein the penis remains in an erect position as shown in FIG. 10. When an erection is no longer desired, the pump 14 is manipulated so that the fluid within the cylinder 12 can flow back into the reservoir 18, to allow the penis to return to the flaccid position shown in FIG. 9.

Pumping fluid into the cylinder builds up the fluid pressure within the cylinder 12 to a level higher than the pressure in the reservoir 18, so that when the pump valve is opened the fluid will have a tendency to flow back into the reservoir 18. The elastic spring characteristic of the sheath 34 pulls the inflatable member 30 toward the base 36. Consequently, the spring force of the sheath 34 creates a reverse pressure within the inner cavity 32, to accelerate the flow of the fluid into the reservoir 18. The reverse pressure created by the sheath 34 is large enough to overcome the static head pressure, which may exist because the reservoir 18 is typically at a higher elevation than the cylinders 12. The sheath 34 insures that the cylinders 12 move all the way back into the retracted position and are not partially extended because of the static head pressure created by the elevation of the reservoir 18.

While certain exemplary embodiments have been described in detail and shown in the accompanying drawings, it is to be understood that such embodiments are merely illustrative of and not restrictive on the broad invention, and that this invention not be limited to the specific constructions and arrangements shown and described, since various other modifications may occur to those skilled in the art.

I claim:

1. A method for assembling a penile prosthesis cylinder, comprising the steps of:
   providing:
      an inflatable member;
      a bellows attached to said inflatable member at one end thereof;
      a base member attachable to said bellows at the other end thereof;
      a sheath extending from said base member to said inflatable member and being adapted to fit around said bellows and attach to said inflatable member;
   rolling up said sheath onto said base member;
   attaching said bellows to said base member;
   unrolling said sheath such that said sheath surrounding the exterior of said bellows; and,
   attaching said sheath to said inflatable member.

2. The method as recited in claim 1, wherein said sheath is attached to said inflatable member by an adhesive.

3. The method as recited in claim 2, further comprising the step of creating a vacuum within said sheath after said bellows is attached to said base member and before said sheath is unrolled, and the additional step of releasing said vacuum within said sheath after said sheath is attached to said inflatable member.

4. The method as recited in claim 3, wherein said step of attaching said bellows to said base member includes inserting a stem of said bellows into a groove of said base member.

5. The method as recited in claim 4, wherein said groove has at least one protrusion adapted to press against said stem and attach said bellows to said base member.

6. An implantable penile prosthesis, such that the penis can be inflated into an erect position and deflated into a flaccid position, comprising:
   an inflatable member disposed on a distal end of said prosthesis;
   an inflatable bellows attached to said inflatable member, said bellows being expandable during inflation such that the prosthesis lengthens when erect;
   a base member attached to said bellows; and,
   a sheath that extends from said base member and is attached to said inflatable member, said sheath being constructed to have a yield pressure of less than 12 psi and to bias said inflatable member toward said base member, wherein the penis is moved into the flaccid position when said bellows is deflated.

7. An implantable penile prosthesis comprising:
   at least one cylinder having
      an inflatable member, wherein said inflatable member increases in both length and girth when said inflatable member is inflated;
      an inflatable bellows attached to said inflatable member, said bellows and said inflatable member being constructed to support the penis in the erect position when inflated;
      a base member attached to said bellow;
      a sheath that extends from said base member and is attached to said inflatable member, said sheath being constucted to have a yield pressure of less than 12 psi and to bias said inflatable member toward said base member such that the penis is moved into the flaccid position when said bellows is deflated;
   a reservoir adapted to provide fluid to said bellows and said inflatable member; and
   a pump connected to said bellows and said reservoir, said pump being constructed to transfer fluid between said reservoir and said cylinder, wherein said bellows and said inflatable member are inflated when fluid is transferred to said cylinder and said bellows and said inflatable member are deflated when fluid is transferred from said cylinder.

8. The prosthesis as recited in claim 7, wherein said base member has a bore and a port that provide fluid communication between said bellows and said pump.

9. A method for inflating a male penis into an erect position and deflating the penis into a flaccid position, comprising:
   providing at least one cylinder within the penis, each said cylinder having:
      an inflatable member disposed on a distal end of said prosthesis, wherein said inflatable member increases in both length and girth when said inflatable member is inflated;
      an inflatable bellows attached to said inflatable member, said bellows being expandable during inflation such that the prosthesis lengthens when erect;
      a base member on the proximal end of said prosthesis and attached to said bellows; and
      a sheath that extends from said base member and is attached to said inflatable member, said sheath being constructed to bias said inflatable member toward said base member by providing a retracting force when stretched, wherein the penis is moved into the flaccid position when said bellows is deflated;
   providing a pump that is operatively connected to said bellows, said pump being constructed to transfer fluid to said bellows such that said bellows can be inflated, said pump further being constructed to allow fluid to be transferred from said bellows such that said bellows can be deflated;
   pumping said pump such that fluid is transferred to said bellows to increase an internal pressure inside said bellows of approximately 12 psi to exceed said retracting force of said sheath until the penis is in the erect position and inflates said bellows and moves said inflatable member in a distal direction; and
   manipulating said pump such that fluid can transfer from said bellows until the penis is in the flaccid position, wherein said sheath pulls said inflatable member toward said base member when said bellows is deflated.

* * * * *